(12) United States Patent
Gliere et al.

(10) Patent No.: US 9,335,259 B2
(45) Date of Patent: May 10, 2016

(54) HELMHOLTZ TYPE DIFFERENTIAL ACOUSTIC RESONATOR DETECTION DEVICE

(71) Applicant: Commissariat A L'Energie Atomique et aux Energies Alternatives, Paris (FR)

(72) Inventors: Alain Gliere, Grenoble (FR); Salim Boutami, Grenoble (FR); Mickael Brun, Eybens (FR); Pierre Labeye, Grenoble (FR); Sergio Nicoletti, Sinard (FR); Justin Rouxel, Saint-Martin-d'Heres (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 0 days.

(21) Appl. No.: 14/677,222

(22) Filed: Apr. 2, 2015

(65) Prior Publication Data
US 2015/0285737 A1    Oct. 8, 2015

(30) Foreign Application Priority Data

Apr. 8, 2014    (FR) ...................................... 14 53101

(51) Int. Cl.
*G01N 21/00* (2006.01)
*G01N 21/3504* (2014.01)
(Continued)

(52) U.S. Cl.
CPC ............ *G01N 21/3504* (2013.01); *G01N 21/03* (2013.01); *G01N 21/0303* (2013.01);
(Continued)

(58) Field of Classification Search
CPC ...................................... G01N 21/00

USPC .......................................... 356/437
See application file for complete search history.

(56) References Cited

U.S. PATENT DOCUMENTS 5,157,461 A * 10/1992 Page ...................... G01C 19/72
                                                    356/462
7,304,732 B1   12/2007 Polcawich et al.

FOREIGN PATENT DOCUMENTS

EP    2 402 735 A2    1/2012
EP    2 515 096 A1    10/2012
(Continued)

OTHER PUBLICATIONS

French Preliminary Search Report issued Jan. 14, 2015 in French Application 14 53101, filed on Apr. 8, 2014.
(Continued)

*Primary Examiner* — Roy M Punnoose
(74) *Attorney, Agent, or Firm* — Oblon, McClelland, Maier & Neustadt, L.L.P.

(57) ABSTRACT

Microelectronic photoacoustic detection device comprising:
- a substrate comprising cavities forming a Helmholtz differential acoustic resonator;
- acoustic detectors coupled to the chambers of the resonator;
- a light source;
- a waveguide comprising a first end coupled to the light source and a second end coupled to a first chamber;
- in which the second end comprises, at the interface with the first chamber, a width greater than that of the first end and that of the given wavelength, and/or in which the device comprises a diffraction grating arranged in the second end and capable of diffracting a first part of the beam towards a lower reflective layer arranged under the second end and a second part of the beam towards an upper reflective layer arranged at an upper wall of the first chamber.

14 Claims, 4 Drawing Sheets

(51) Int. Cl.
*G01N 21/03* (2006.01)
*H01S 5/026* (2006.01)
*G01N 29/036* (2006.01)
*G01N 29/22* (2006.01)
*G01N 29/24* (2006.01)
*G01N 21/17* (2006.01)

(52) U.S. Cl.
CPC .......... *G01N21/1702* (2013.01); *G01N 29/036* (2013.01); *G01N 29/222* (2013.01); *G01N 29/2425* (2013.01); *H01S 5/026* (2013.01); *G01N 2021/1704* (2013.01); *G01N 2021/1708* (2013.01); *G01N 2201/0612* (2013.01); *G01N 2201/08* (2013.01); *G01N 2291/021* (2013.01)

(56) References Cited

FOREIGN PATENT DOCUMENTS

WO     WO 03/083455 A1    10/2003
WO     WO 2008/074442 A1    6/2008

OTHER PUBLICATIONS

Samara L. Firebaugh et al. "Miniaturization and Integration of Photoacoustic Detection", Journal of Applied Physics, vol. 92, No. 3, 2002, 9 pages.

B.Ben Bakir et al. "Electrically Driven Hybrid Si/III-V Fabry-Perot Lasers Based on Adiabatic Mode Transformers", Opt. Express, vol. 19, No. 11, 2011, 9 pages.

\* cited by examiner

HELMHOLTZ TYPE DIFFERENTIAL ACOUSTIC RESONATOR DETECTION DEVICE

TECHNICAL FIELD AND PRIOR ART

The invention relates to the field of photoacoustic detection devices, and especially that of integrated gas sensors making use of a photoacoustic effect to measure the concentration of some gaseous elements.

The principle of measuring a gas by photoacoustic effect is based on the excitation of an acoustic wave in the gas by a powerful light source such as a pulsed or amplitude or wavelength modulated laser. The wavelength of the mid-infrared radiation (MIR) emitted by the laser is chosen to interact with the molecules of the gas to be detected. Since the emission of the light source is variable over time, the energy absorbed by the gaseous molecules is restored in the form of a transitory heating which generates a pressure wave, itself measured by an acoustic detector.

Detection is improved by confining the gas in a cavity and by modulating the laser to an acoustic resonance frequency of the cavity. The amplitude of the acoustic wave obtained is directly linked to the concentration of the gaseous compound searched for in the gas present in the excited cavity.

The detection efficiency is based to a large extent on the efficient coupling of the luminous flux coming from the laser with the gas contained in the resonant cavity because the signal measured is proportional to the energy absorbed, then dissipated, by the gas.

The document WO 03/083455 A1 describes a photoacoustic measurement device which makes it possible to detect the presence of a gas and comprising a particular structure of photoacoustic cells designated "Differential Helmholtz Resonator" (DHR), or Helmholtz type differential acoustic resonator. Such a resonator comprises two identical chambers connected together by two capillaries.

Acoustic resonance is produced by exciting only one of the two chambers. At resonance, the pressures in the two chambers oscillate in phase opposition. The pressures in the chambers are measured by microphones placed in the two chambers. With such a resonator, the calculation of the difference between the signals coming from each chamber, which corresponds to the useful signal, makes it possible to increase the amplitude of the measured signal and to eliminate part of the surrounding noise, and thus to have in the end a good signal to noise ratio. Another type of differential photoacoustic resonator is described in the document WO 2008/074442 A1.

Such devices nevertheless have the drawbacks of being limited to non-miniaturised laboratory devices, of having limited transmission wavelengths, of being sensitive to temperature variations and to vibrations, and of having considerable constraints of positioning and alignment of their elements to produce them.

A miniaturisation of such a device at the millimetric scale is proposed in the document U.S. Pat. No. 7,304,732 B1. This miniaturisation makes it possible to have a stronger pressure signal produced by the sensor due to the fact that said signal increases when the size of the resonator is reduced. DHR resonators are particularly well suited to miniaturisation and integration on silicon because they are relatively insensitive to the localisation of the thermal energy deposition and because, the pressure being virtually constant in each chamber, it is possible to multiply the number of microphones per chamber to improve the signal to noise ratio.

The document EP 2 515 096 A1 describes a photoacoustic gas detection device comprising a miniaturised photoacoustic resonator integrated on silicon. The structure of said detector is obtained by the implementation of techniques of the field of microelectronics in several substrates bonded together. The manufacturing process imposes placing the MIR waveguide, which makes it possible to inject the optical laser signal into one of the two chambers, in the lower part of the central substrate which is thinned to a thickness determined by the height of the chambers.

The miniaturisation and the integration on silicon of this type of detector nevertheless pose a problem. In fact, the MIR produced by the laser is transmitted up to the chamber excited by a waveguide of section comparable to the wavelength of the radiation. At the inlet of the excited chamber, the beam undergoes a diffraction due especially to the low thickness of the silicon, which leads to a significant divergence of the beam. This divergence of the light beam, allied to the transparency of the silicon (in which is the resonator is manufactured), leads to poor confinement of the light and thus to poor light-gas coupling. This phenomenon is exacerbated by the fact that the luminous flux penetrates near to the bottom of the chamber. Furthermore, this poor confinement may lead to partial illumination of the second chamber (phenomenon of diaphony), which reduces the amplitude of the useful signal obtained.

DESCRIPTION OF THE INVENTION

Thus there is a need to propose a DHR integrated type of photoacoustic detection device, and in which the confinement of the light beam intended to be injected into one of the chambers of the device is improved.

To achieve this, one embodiment proposes a photoacoustic detection device comprising:
  at least one substrate comprising cavities forming a Helmholtz type differential acoustic resonator (or DHR);
  acoustic detectors coupled to two of said cavities forming chambers of the resonator;
  a light source capable of emitting a light beam at at least one given wavelength;
  an optical waveguide comprising a first end optically coupled to the light source and a second end optically coupled to a first of the two chambers;
  in which the second end comprises, at an interface with the first chamber, a width of value greater than that of the width of the first end and greater than that of said at least one given wavelength, and/or in which the photoacoustic detection device comprises at least one diffraction grating arranged in the second end of the waveguide and capable of diffracting a first part of the light beam towards a lower reflective layer arranged under the second end and a second part of the light beam towards an upper reflective layer arranged at an upper wall of the first chamber.

In this photoacoustic detection device, the confinement of the light beam is improved horizontally via the widening of the second end of the waveguide that is optically coupled to the first chamber, which is intended to receive the light beam, due to the fact that said widening makes it possible to reduce or even to cancel the diffraction of the light beam in the direction parallel to said width. The confinement of the light beam is moreover improved vertically thanks to the diffraction grating that makes it possible to diffract the light beam in a specific direction towards the reflective layers, which makes it possible to confine the light beam in the first chamber.

The term "width" is used here and throughout the remainder of the document to designate, with reference to the waveguide, the dimension that lies in a propagation plane of the light beam in the waveguide and which is perpendicular or substantially perpendicular to a direction of propagation of the light beam in the waveguide. More generally, the term "width" designates the dimension which is perpendicular or substantially perpendicular to a direction of propagation of the light beam in the waveguide.

Preferably, the optical waveguide may be such that it operates on the fundamental mode for which the diffraction grating is dimensioned and diffracts at a very precise angle. Such a single mode operation of the optical waveguide is advantageous because it enables better control of the direction of the light beam. If several modes are excited, these modes can diffract in several directions. Nevertheless, in the case of a multimode waveguide, a small index difference between the core and the cladding of the waveguide can make it possible to limit the variation in the effective index of the guide.

Advantageously, the photoacoustic detection device comprises at one and the same time an optical waveguide of which the second end has, at an interface with the first chamber, a width greater than that of the first end and at said given wavelength, and the diffraction grating arranged in the second end of the waveguide and coupled to the lower and upper reflective layers. This configuration makes it possible to improve the horizontal and vertical confinement of the light beam.

The value of the width of the second end is preferably greater than or equal to several times that of said given wavelength.

The "DHR" type detection device is a microelectronic device, that is to say obtained by successive steps of deposition of layers, of etching, and potentially of planarization, implantation and transfer. Such a microelectronic device preferentially occupies, on the substrate, a surface area less than around 25 mm$^2$.

The lower reflective layer corresponds to the lower reflective layer of the optical waveguide.

The upper wall of the first chamber is formed by the upper reflective layer.

The device functions when the waveguide comprises a second end wider than the first end and that it comprises the diffraction grating arranged in the second end of the waveguide. Nevertheless, the device also operates when the waveguide comprises a second end wider than the first end but that it does not comprise the diffraction grating, or instead when the waveguide does not comprise a second end wider than the first end but that the diffraction grating is arranged in said second end.

The ratio between the width of the second end at the interface with the first chamber and the width of the first end may be greater than or equal to 3.

The second end may form a portion of the waveguide of which the width increases from a first value equal to that of the width of the first end up to a second value equal to that of the width of the second end at the interface with the first chamber.

In this case, the width of the second end may increase on a part, called first part, of the second end of which the length may be greater than or equal to around ten times the width of the second end at the interface with the first chamber. The term "length" here designates, with reference to the waveguide, the dimension that lies in the propagation plane of the light beam in the waveguide and which is parallel to the direction of propagation of the light beam in the waveguide (and thus perpendicular to the width defined previously). The terms "thickness" and "height" refer to the dimension which is perpendicular to the width and to the length. Such a progressive increase in the width of the second end of the waveguide makes it possible to conserve well the single mode character of the transmission of the light beam formed by the waveguide.

The diffraction grating may be arranged in a part, called second part, of the second end of which the width may be substantially constant and equal to that at the interface with the first chamber.

The diffraction grating may be arranged at an interface between a core layer of the waveguide and a lower cladding layer of the waveguide, the lower cladding layer being able to be arranged between the core layer and the lower reflective layer.

The diffraction grating may be capable of diffracting the light beam such that the first or the second part of the light beam reaches, after a reflection on the lower reflective layer and/or the upper reflective layer, a bottom wall of the first chamber which is opposite to that in contact with the second end of the waveguide. Thus, the diffraction grating may be dimensioned, especially as regards the pitch of the grating, such that the path of the light beam is maximised in the first chamber for the first or the second part of the light beam. Although this configuration is advantageous, it is entirely possible that the diffraction grating is not dimensioned so that the first or the second part of the light beam reaches, after a reflection on the lower reflective layer and/or the upper reflective layer, the bottom wall of the first chamber.

The acoustic detectors may be arranged in a first substrate and be coupled to the chambers of the resonator formed in a second substrate made integral with the first substrate, volumes of the chambers being able to communicate together via capillaries formed in a third substrate made integral with the second substrate.

In a variant, the acoustic detector may be arranged in a first substrate and be coupled to the chambers of the resonator formed in a second substrate made integral with the first substrate, volumes of the chambers communicating together via capillaries formed in the second substrate, the second substrate having a thickness less than 300 μm. Thus, by forming the capillaries and the chambers in a same substrate, it is possible to reduce the thickness of the chambers, and potentially that of the capillaries, to a value less than 300 μm.

The device may further comprise trenches filled with at least one optically reflective material and arranged around the first chamber, and especially around lateral walls of the first chamber. Such trenches contribute to improving the horizontal confinement (that is to say in the direction parallel to the width of the waveguide) of the light beam.

The two chambers may comprise dimensions different to each other. Such asymmetry of said chambers can make it possible to optimise the phase opposition of the acoustic signals measured in the two chambers.

The acoustic detectors may comprise beam type piezoresistive microphones.

Another embodiment relates to a gas detection device, comprising at least one photoacoustic detection device as described previously and further comprising gas inlet and outlet channels communicating with the chambers of the resonator, for example through the intermediary of capillaries, and in which the wavelength intended to be emitted by the light source corresponds to an absorption wavelength of a gas intended to be detected. Such a device thus forms a low cost gas sensor being able to be used for example in the field of gas detection outside (detection of pollution, measurement of greenhouse gas effect, etc.) or inside (interior air quality, air conditioning, detection of substances in an interior space, etc.).

Another embodiment relates to a method of producing a photoacoustic detection device, comprising at least the steps of:

forming, in at least one substrate, an optical waveguide comprising a first end and a second end, forming a light source capable of emitting a light beam at at least one given wavelength and such that the light source is optically coupled to the first end of the waveguide, forming, in said at least one substrate, cavities forming a Helmholtz type differential acoustic resonator, two of said cavities forming chambers of the resonator such that a first of the two chambers is optically coupled with the second end of the waveguide, coupling acoustic detectors with the chambers of the resonator, in which the second end comprises, at an interface with the first chamber, a width of value greater than that of the width of the first end and greater than that of said at least one given wavelength, and/or in which the method comprises the formation of at least one diffraction grating in the second end of the waveguide capable of diffracting a first part of the light beam towards a lower reflective layer arranged under the second end and a second part of the light beam towards an upper reflective layer arranged at an upper wall of the first chamber.

BRIEF DESCRIPTION OF THE DRAWINGS

The present invention will be better understood on reading the description of embodiment examples given for purely illustrative purposes and in no way limiting and by referring to the appended drawings in which.

The different parts represented in the figures are not necessarily according to a uniform scale in order to make the figures more legible.

The different possibilities (variants and embodiments) must be understood as not being exclusive of each other and may be combined together.

DETAILED DESCRIPTION OF PARTICULAR EMBODIMENTS

Figure 1:
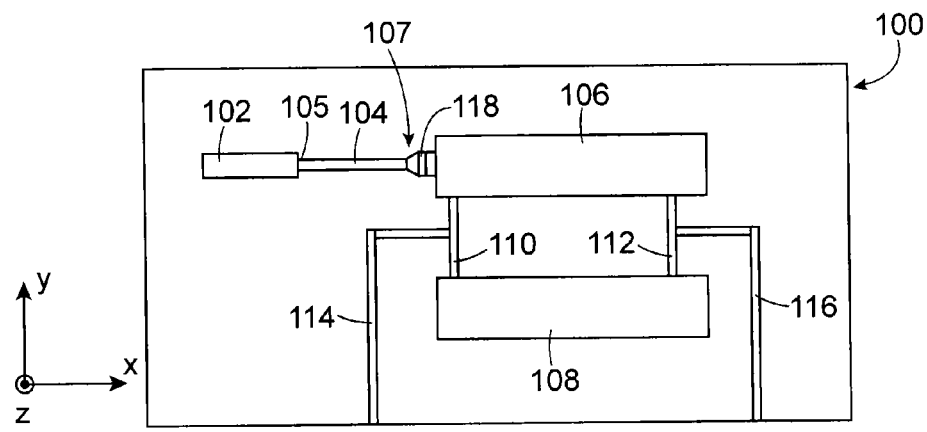
FIG. 1 schematically represents a photoacoustic detection device according to a particular embodiment, FIG. 2 schematically represents an embodiment example of a second end of the waveguide of the photoacoustic detection device, FIG. 3 schematically represents a part of the photoacoustic detection device.

Reference will firstly be made to FIG. 1 which schematically represents a photoacoustic detection device 100 according to a particular embodiment. This photoacoustic detection device 100 corresponds to a gas detection device.

The device 100 comprises a powerful light source 102, here corresponding to a laser. This laser may correspond to a laser of QCL (quantum cascade laser) type emitting in the MIR field, for example at wavelengths comprised between around 3 μm and 10 μm. Although not represented, the device 100 also comprises an electrical supply of the light source 102 as well as means of modulating the light beam emitted to an acoustic resonance frequency of the cavity into which the beam is intended to be sent. Compared to the use of a light source 102 which would not be collimated, the use of a collimated light source 102 in the device 100 makes it possible to considerably increase the signal/noise factor, for example by a factor 2. The window noise corresponds to the parasitic acoustic signal that all solid parts emit when they are struck by the modulated light wave.

The light beam emitted is then transmitted into an optical waveguide 104, advantageously single mode and for example formed of a Si/Ge/Si stack, or SiN/Si/SiN stack, or more generally a stack of a first material of optical index $n_1$, of a second material of optical index $n_2 > n_1$, and of a third material of optical index $n_3 < n_2$ (with $n_3$ potentially equal to $n_1$), these three materials being transparent to the wavelength emitted by the light source 102. The optical waveguide 104 comprises a first end 105 optically coupled to the light source 102. The coupling between the light source 102 and the waveguide 104 may be carried out directly, for example by evanescent waves, or via the use of a coupler (not represented in FIG. 1) for example of taper type (forming an extruded elongated trapeze).

The device 100 also comprises elements corresponding to cavities, or hollowings out, formed in one or more substrates integral with each other, and forming a Helmholtz type differential acoustic resonator (DHR). These elements are:

a first chamber 106 in which the gas to be detected is intended to be excited by the light beam emitted by the source 102, and of which an inlet face intended to receive the light beam is optically coupled to a second end 107 of the waveguide 104;

a second chamber 108;

two capillaries 110 and 112 enabling the volumes of the chambers 106 and 108 to communicate together.

The device 100 also comprises an inlet channel 114 making it possible to feed the gas into the chambers 106 and 108 via the capillary 110, and an outlet channel 116 making it possible to evacuate the gas outside of the chambers 106 and 108 via the capillary 112. In FIG. 1, the inlet 114 and outlet 116 channels are connected to the capillaries 110 and 112 substantially at the level of the middle of said capillaries 110, 112. Acoustic detectors (not visible in FIG. 1) such as miniaturised piezoresistive microphones, for example of membrane or beam type, are also coupled to the chambers 106, 108 in order to carry out pressure measurements in the chambers 106, 108. Each of the chambers 106, 108 may be coupled to one or more microphones, for example up to eight microphones per chamber. Finally, the device 100 also comprises electronic circuits for processing the signals delivered by the acoustic detectors which are not represented in FIG. 1.

The operating principle of the device 100 is similar to that described in the document EP 2 515 096 A1 and is thus not described in detail herein.

In order to confine the light beam in the first chamber 106 and thus to improve the light-gas coupling occurring in the first chamber 106, the device 100 comprises an element making it possible to control the horizontal divergence (along the y axis represented in FIG. 1) of the light beam at the interface between the first chamber 106 and the second end 107 of the waveguide 104, and an element making it possible to control the vertical divergence (along the z axis represented in FIG. 1) of the light beam at said interface.

Figure 2:
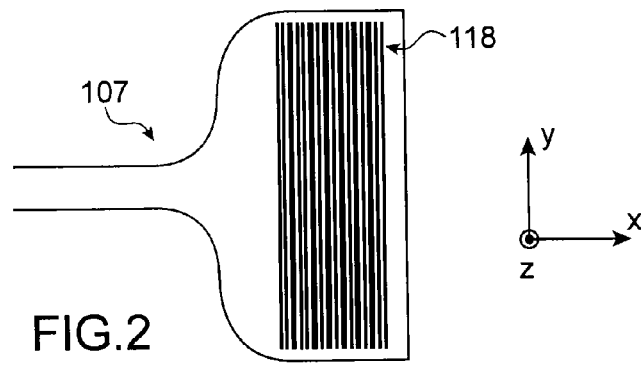

Thus, at the interface with the first chamber 106, the second end 107 of the waveguide 104 is formed such that its width (dimension along the y axis), that is to say its dimension situated in the propagation plane of the light beam and which is perpendicular to the direction of propagation of the light beam, increases in order to achieve the horizontal confinement of the light beam due to the fact that this increase in the width of the second end 107 of the waveguide 104 leads to a reduction in diffraction in the direction of said widening. This widening of the second end 107 of the waveguide 104 is represented schematically in FIG. 2 that represents a top view of the waveguide 104 at its second end 107 which is located at the interface with the first chamber 106. This widening of the second end 107 of the waveguide 104 is progressive and preferably such that it conserves the single mode character of the transmission of the light beam up into the first chamber 106. Such a widening may be qualified as adiabatic when the effective index varies linearly and when it makes it possible to conserve the single mode character while minimising the length of said second end 107. The second end 107 of the waveguide 104 may for example have an initial width, equal to that of the remainder of the waveguide 104 and especially equal to that at the first end 105, equal to around 3 μm, or comprised between around 3 μm and 8 μm, and a final width (width at the interface with the first chamber 106) equal to around 30 μm, or comprised between around 30 μm and 40 μm or between around 30 μm and 50 μm, that is to say here a ratio between the final width and the initial width comprised between around 10 and 13.33. The ratio between the final width and the initial width is for example comprised between around 3 and 20, and for example around 10. In order to conserve the single mode character of the transmission of the light beam up to the chamber 106, this widening is for example made over a length of around 300 μm, or comprised between around 50 μm and 500 μm. The value of the initial width may be of the order of that of the wavelength of the light beam emitted to achieve a single-mode guiding of said light beam, and the value of the final width is greater than that of said wavelength to obtain a horizontal confinement of the light beam.

The control of the vertical divergence of the light beam is carried out thanks to a diffraction grating 118 formed at the second end 107 of the waveguide 104, and more particularly at a part of this second end 107 of which the width is substantially constant and equal to that at the interface with the first chamber 106. This control of the vertical divergence of the light beam is also achieved thanks to a lower reflective layer 120 arranged under the second end 107 and extending up to the level of the inlet face of the first chamber 106, and thanks to an upper reflective layer 122 arranged at the upper wall of the chamber 106. The diffraction grating 118 comprises a series of parallel grooves, or slits, formed in the core layer of the waveguide 104 (which is for example germanium-based), the grooves being filled with a material of which the refractive index is less than that of the material of the core layer, for example with $SiO_2$, silicon nitride, etc. The diffraction grating 118 is for example formed over a length of around 1 mm to obtain a sufficient decoupling efficiency of the order of 60%.

Figure 3:
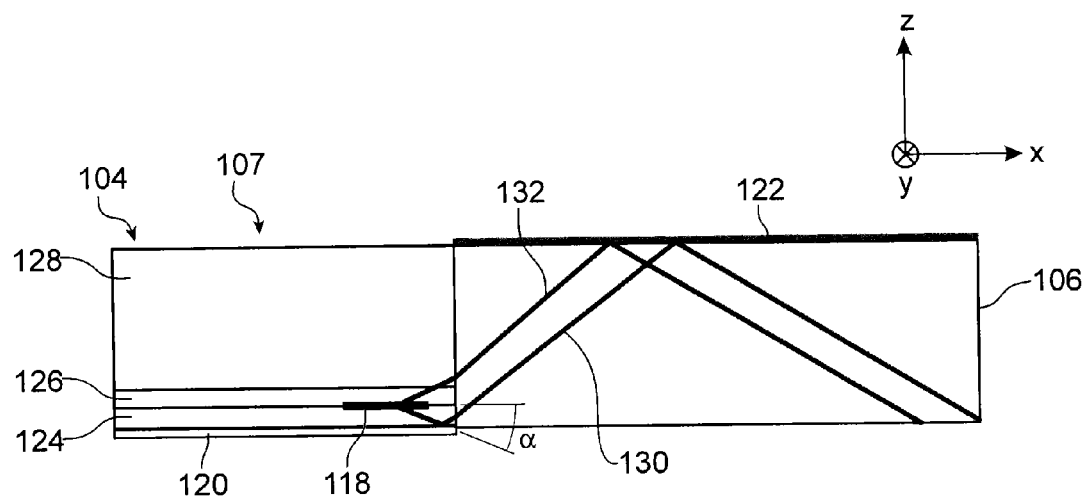

FIG. 3 represents the second end 107 of the waveguide 104 formed by a first silicon layer 124, on which is arranged a core layer 126, for example made of germanium, itself covered by a second layer 128 of silicon, the layers 124 and 128 forming the upper and lower cladding layers of the waveguide 104. In a variant, the core layer 126 could be made of silicon, and the layers 124 and 128 made of SiN. The diffraction grating 118 is preferably formed at the lower part of the core layer 126 which is in contact with the lower cladding layer 124 in order to avoid, while the diffraction grating 118 is being formed, the implementation of an epitaxy of the core material on a non-flat silicon layer. Nevertheless, it is possible that the diffraction grating 118 is formed at the upper part of the core layer 126 which is in contact with the upper cladding layer 128. In the configuration represented in FIG. 3, one or more acoustic detectors (not represented in this figure) are coupled to the first chamber 106, at the lower wall of the chamber 106, and to the second chamber 108.

A first part 130 of the light rays diffracted by the diffraction grating 118 are oriented downwards, that is to say towards the lower reflective layer 120, and a second part 132 of the light rays diffracted by the diffraction grating 118 are oriented upwards, that is to say towards the upper reflective layer 122. The pitch of the diffraction grating 118 is calculated so that the diffraction angle of the rays 130 and 132 (said angle being the same for the rays 130 and 132) is such that the rays 130 oriented downwards or the rays 132 oriented upwards pass through the whole length of the first chamber 106, which is for example around 2.6 mm, in order to maximise the path length of the light radiation in the first chamber 106. In the example represented in FIG. 3, this diffraction angle is such that the rays 130, which reflect firstly on the lower reflective layer 120, pass through the whole length of the first chamber 106, said passing through of the first chamber 106 being realised with a reflection on the upper reflective layer 122 in order to maximise the path length in the first chamber 106. In a variant, the diffraction grating 118 could be such that the diffraction angle formed by the rays diffracted by the grating 118 enables the rays 132 to pass through the whole length of the first chamber 106.

Thanks to the widening of the second end 107 of the waveguide 104 and to the presence of the diffraction grating 118 and the reflective layers 120 and 122, a confinement of the light rays in the first chamber 106 is obtained, thereby improving the light-gas coupling in the first chamber 106 and also avoiding the second chamber 108 being partially illuminated due to the divergence of the beam.

An example of optical dimensioning of the elements of the device 100 is described below. This example is calculated for a first chamber 106 intended to receive light rays which is of rectangular shape and which comprises a width and a height each equal to around 300 μm, and a length equal to around 2.6 mm. Considering the example described previously with reference to FIG. 3 in which the path of the rays 130 (that is to say the rays diffracted towards the lower reflective layer 120 then towards the upper reflective layer 122) is maximised, the desired value of the diffraction angle α with which the light rays are diffracted by the diffraction grating 118 is firstly calculated in such a way that said rays pass through the whole length of the chamber 106. The value of the diffraction angle α (angle measured with respect to the axis of the waveguide 104) is calculated from the following transcendent equation:

$$\sin(\alpha) = \frac{n_2}{n_1} \sin\left[a\tan\left(\frac{2H - h_0 - d\tan(\alpha)}{d}\right)\right] \quad (1)$$

with $n_2$ corresponding to the refractive index in the chamber 106, that is to say here equal to around 1, $n_1$ corresponding to the refractive index of the material of the first layer 124 in which the rays are diffracted, and equal to around 3.4 in the case of a first layer 124 made of silicon, H the height of the chamber 106, here equal to 300 μm, $h_0$ the thickness of the first layer 124, here equal to around 10 µm, d the distance between the centre of the diffraction grating 118 and the inlet face of the chamber 106, that is to say half the length of the diffraction grating 18, here equal to around 0.5 mm.

The diffraction angle formed by the other rays (the rays 132 in the example of FIG. 3) will be similar to that for the rays of which the path is maximised in the first chamber 106. Nevertheless it is advisable to have a diffraction angle sufficiently small so that these other rays are directed all the same towards the inlet face of the chamber 106.

The pitch Λ of the diffraction grating 118 is then calculated according to the following equation:

$$\Lambda = \frac{m\lambda}{n_{eff} - n_{Si}\cos\alpha} \quad (2)$$

with m corresponding to the order of diffraction and which is equal to 1 for the calculation of the pitch of the grating, λ corresponding to the wavelength emitted by the light source 102, $n_{Si}$ corresponding to the refractive index of silicon (more generally of the material of the lower layer 124), α corresponding to the diffraction angle, $n_{eff}$ corresponding to the effective index, that is to say the index seen by the mode (at the propagation velocity of the mode in the guide).

The light source 102 emits a laser radiation in the MIR field at a wavelength λ equal to 4 µm. For a diffraction angle equal to 3.7° in silicon and equal to 12.5° in air, a pitch of 39 µm is obtained for α=4°, $n_{Si}$=3.4 and $n_{eff}$=3.5. When this diffraction grating 118 is formed over a length of around 1 mm on a waveguide 104 of which the width goes from 3 µm to 30 µm over a length of around 300 µm, an absorption of around 11.1 mW per incident W (power of the beam entering the chamber) in the $CO_2$ contained in ambient air is obtained, whereas an absorption of 4.6 mW per incident W is obtained without these elements enabling the confinement of the light beam. A factor of around 2.5 is obtained on the proportion of signal transmitted in the first chamber 106 thanks to the confinement means used. Furthermore, the widening of the second end 107 of the waveguide 104 has the other effect of reducing diaphony due to the fact that the second chamber 108 is not or is little illuminated by the light beam sent into the first chamber 106.

The filling rate of the grooves in the diffraction grating 118 affects the decoupling realised. It is determined by simulation and is for example equal to around 50%.

According to an embodiment variant, the device 100 may comprise chambers 106 and 108 not having similar dimensions. In fact, given that the device 100 is a miniaturised device produced via the implementation of microelectronics techniques and MEMS/NEMS systems, a phase opposition may appear between the pressure signals measured in the two chambers 106 and 108 which is imperfect when the dimensions of the chambers 106 and 108 are identical. The subtraction of these two signals which is carried out to obtain the desired measurement is then not optimal. In order to improve this opposition of phases, it is possible that the widths and/or the lengths of the chambers 106 and 108 are different to each other. An optimisation by simulation (for example by resolving the equation of the pressure field in the device 100, with chambers 106 and 108 of different sizes), for example via a calculation by the finite elements method, leads to the optimal ratio of the dimensions of the chambers 106 and 108.

Figure 4:
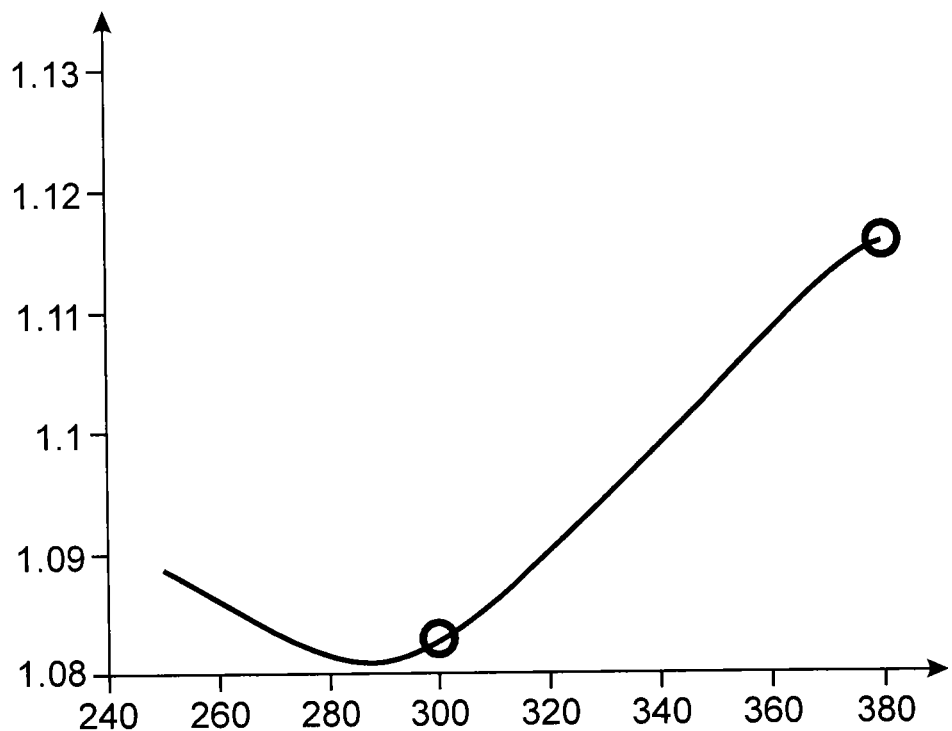
FIG. 4 represents the amplitude of the signal measured by the gas detection device as a function of the difference between the widths of the chambers of the device.

The curve represented in FIG. 4 corresponds to the amplitude of the signal obtained (in Pa, and corresponding to the difference in the pressures measured by the acoustic detectors in the two chambers 106 and 108) as a function of the width of the second chamber 108 (in µm), for a first chamber 106 of width equal to around 300 µm. It may be seen in this figure that the maximum amplitude of the signal is not obtained for a second chamber 108 having a width similar to that of the first chamber 106, that is to say equal to around 300 µm, but for a width greater than 300 µm in this particular case. In other cases, the maximum amplitude of the signal may be obtained for a second chamber 108 having a width less than that of the first chamber 106.

The device 100 is for example formed by the assembly of three substrates:
- a first lower substrate comprising the acoustic detectors intended to be coupled to the chambers 106 and 108, and in which are formed the inlet and outlet channels 114 and 116,
- a second middle substrate in which are formed the light source 102, the waveguide 104, the diffraction grating 118 and the chambers 106 and 108;
- a third upper substrate forming the cover of the chambers 106 and 108 and in which are also formed the capillaries 110 and 112.

In a variant, the device 100 may be formed with only two substrates. In this case, the capillaries 114 and 116 are formed in the second substrate in which the chambers 106 and 108 are formed. The capillaries 114 and 116 may in this case have a height similar to that of the chambers 106 and 108. By only resorting to two substrates instead of three, it is possible to reduce the thickness of the chambers 106 and 108 to a value less than around 300 µm on account of the fact that such a configuration with two substrates avoids the use of a middle substrate of which the thickness must correspond to the thickness of the chambers and which is difficult to handle when said thickness is less than around 300 µm. By etching the capillaries and the chambers in a same substrate with a depth which is less than the total thickness of the substrate (due to the fact that in this case, the upper walls of the chambers and the capillaries are formed by a non-etched part of the second substrate and not by a third substrate transferred onto the second middle substrate), it is possible to have chambers 106 and 108 of which the height is low while conserving a greater total thickness for the substrate enabling a handling of the substrate without risk of breakage. A device 100 formed with only two substrates enables the formation of chambers 106 and 108 of which the thickness is for example comprised between around 300 µm and 100 µm, but remains compatible with the formation of chambers 106 and 108 of thickness greater than around 300 µm.

Figure 5:
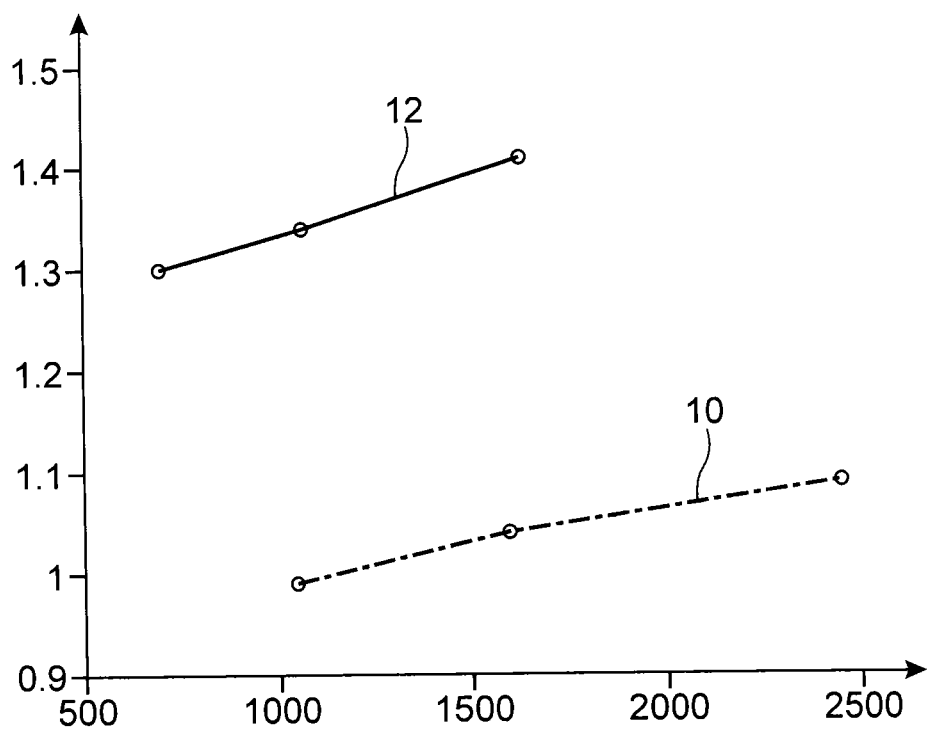
FIG. 5 represents the amplitude of the signal measured by the gas detection device for different distances between the capillaries and for chambers of different dimensions.

This reduction in the thickness of the chambers 106 and 108 makes it possible to obtain an output signal of greater amplitude. Curve 10 represented in FIG. 5 corresponds to the amplitude of the signal obtained (in Pa, and corresponding to the difference in pressures measured by the acoustic detectors in the two chambers 106 and 108) as a function of the distance between the capillaries 110 and 112 for a device 100 of which the chambers 106 and 108 have a thickness equal to around 300 µm, and curve 12 corresponds to the amplitude of the signal obtained for a device 100 of which the chambers 106 and 108 have a thickness equal to around 200 µm. FIG. 5 clearly illustrates the fact that the amplitude of the signal represented by curve 12 is greater than that obtained for the signal represented by curve 10. Furthermore, the amplitude of the output signal is impacted by the distance between the capillaries 110 and 112 on account of the energy losses in the limit layers and the particular form of the flow of the gas.

An example of method of producing the photoacoustic detection device 100 is described in relation to FIGS. 6A to 6I which represent schematic sectional views of the elements of the device 100. In this embodiment example, the device 100 is formed via an assembly of three substrates.

FIGS. 6A to 6F represent the steps relating to the formation of the second middle substrate which comprises the waveguide 104, the diffraction grating 118 and the chambers 106 and 108, as well as other elements such as electrical contacts of the acoustic detectors. FIGS. 6G to 6I represent the later steps of the method during which the second middle substrate is made integral with the first lower substrate and with the third upper substrate forming especially the cover of the chambers 106 and 108.

Figure 6A:
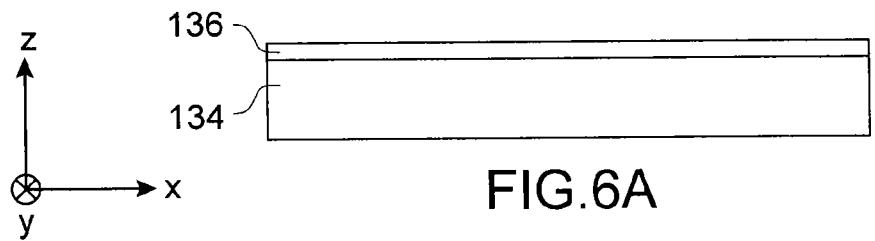
FIGS. 6A to 6I represent the steps of a method of producing a photoacoustic detection device, Identical, similar or equivalent parts of the different figures described hereafter bear the same numerical references so as to make it easier to go from one figure to the next.

As represented in FIG. 6A, the second middle substrate corresponds to a bulk semi-conductor substrate 134, here silicon-based. The material at an upper face of the substrate 134 corresponds to the material which will form the upper cladding layer 128 of the waveguide 104. Then a first deposition or an epitaxial growth is carried out of a layer 136 comprising a material with refractive index greater than that of the material of the substrate 134 and transparent to the wavelength(s) intended to be transmitted by the waveguide 104, here a material transparent in the infrared and for wavelengths comprised between around 3 μm and 10 μm. A part of this layer 136, for example formed by epitaxy, is intended to form the core layer 126 of the waveguide 104. The thickness and the material of the layer 136 are chosen so that the waveguide 104 can carry out a single-mode guiding of the light beam.

The thickness of the layer 136 is for example comprised between around 1 and 10 μm, and is for example germanium-based or SiGe-based depending on the material desired to form the core layer 126 of the waveguide 104. In the case of a SiGe-based layer 136, the germanium composition of the SiGe, that is to say the proportion of germanium in the SiGe, may be constant or instead vary throughout the thickness of the layer 136 to form a core layer comprising an index gradient according to a profile (in the direction of the thickness of the layer 136) being able to be triangular or trapezoidal. For example, for a waveguide 104 intended to transmit a wavelength of 4.5 μm, the germanium composition within the layer 136 may form, throughout the thickness of this layer, a triangular profile over a thickness of around 3 μm with a germanium composition extending from 0% (at the upper and lower faces of the layer 136) to 40% in the middle of the layer 136, these variations being for example linear throughout the thickness of the layer 136. In a variant, the layer 136 may be SiGe-based and comprise a constant germanium concentration throughout the thickness of this layer and for example equal to 40%, the layer 136 having in this case a thickness for example equal to 2.7 μm.

The diffraction grating 118 is then formed at the upper face of the layer 136. To achieve this, a lithography and an RIE (reactive ion etching) or DRIE (deep reactive ion etching) type etching are implemented at the place provided for the diffraction grating 118, that is to say at the part of the second end 107 of the waveguide 104 that is intended to be located near to the place provided for the first chamber 106 which is intended to receive the light beam. The photolithography and the etching are implemented such that they form, in a part of the thickness of the layer 136 (the thickness of the layer 136 being for example comprised between around 1 μm and 10 μm), the grooves of the diffraction grating of which the dimensions and the spacing correspond to the calculated values in order to obtain the desired diffraction angle, as described previously.

Figure 6B:
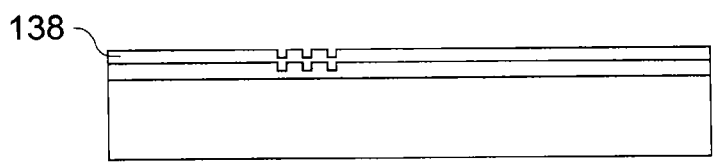

After this etching, a layer 138 of material of which the refractive index is less than that of the material of the layer 136, such as $SiO_2$, SiN or $Si_3N_4$, is formed, for example by deposition, on the layer 136 and in the patterns etched through the upper face of the layer 136 to form the diffraction grating 118 (FIG. 6B).

The layer 138 is then planarized, for example via chemical-mechanical planarization (CMP) with stoppage on the upper face of the layer 136, in order that the low index material is only conserved in the patterns of the diffraction grating 118.

The core of the waveguide 104 is then formed by lithography and etching of the layer 136 in order that at least one part of the remaining portions of the layer 136 form the core layer 126 of the waveguide 104. This etching is not visible in FIGS. 6A-6I. This etching is carried out through a part or the totality of the thickness of the layer 136 depending on the structure desired to form the core of the waveguide 104. When the waveguide 104 comprises a core layer 126 made of SiGe with triangular shaped index gradient, the layer 136 may be etched such that the remaining portion forming the waveguide 104 has a width equal to around 3.3 μm, or comprised between around 3.3 μm and 8 μm, which allows it to carry out a single-mode guiding of a light beam of wavelength equal to 4.5 μm. As described previously, the second end 107 of the waveguide 104 is formed with progressive widening in order to enable a transmission of the fundamental mode of the light beam for which the diffraction grating 118 is optimised while reducing the diffraction of the beam along the direction of the widening, and thus improving the horizontal confinement of the light beam.

Figure 6C:
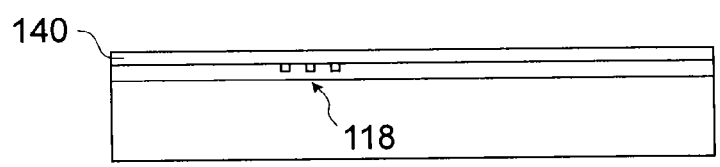

The remaining portion(s) of the layer 136 are then covered by the deposition or the epitaxial growth of a layer 140 intended to form the lower cladding layer 124 of the waveguide 104, which thus comprises a material of lower refractive index than that of the core layer, and for example silicon-based in the case of a core layer made of SiGe. This layer 140 is then planarized for example via CMP in order that the upper face of the layer 104 forms a flat surface (FIG. 6C).

In a variant, the formation of the diffraction grating 118 could be simplified by implementing a single lithography step, a single etching step and a single CMP step.

Materials other than silicon and germanium may be used to form the waveguide 104, said materials having nevertheless to enable a transmission of the wavelength of the light beam and be compatible with the techniques implemented to form the device 100. It is nevertheless possible to form the waveguide 104 with a core layer made of silicon and arranged between two cladding layers made of SiN.

Figure 6D:
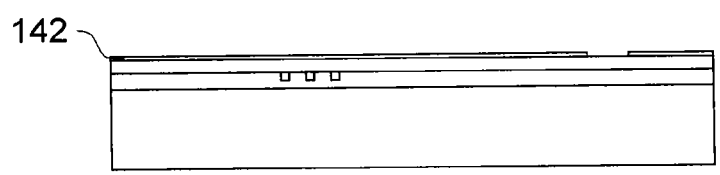
Figure 6E:
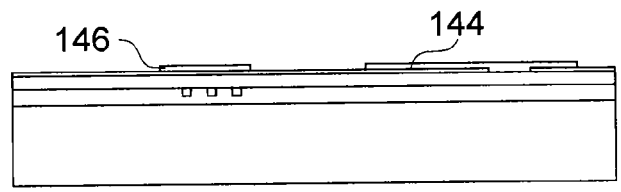

A dielectric layer 142 is then deposited on the layer 140, for example $SiO_2$-based and of thickness equal to around 1 μm, or SiN-based or $Al_2O_3$-based. Said dielectric layer 142 is etched at emplacements intended to form electrical contacts pick-up of the acoustic detectors of the device 100 (FIG. 6D). An electrically conducting layer, for example metal-based, is then deposited on the dielectric layer 142. This electrically conducting layer is for example AlSi-based (comprising around 1% of silicon). The electrically conducting layer is then etched in order that the remaining portions 144 of this layer, filling especially the places previously etched in the dielectric layer 142, form the electrical contacts of the acoustic detectors. At least one other remaining portion 146 of this electrically conducting layer may also be conserved in order to form the lower reflective layer 120, especially when the material of the dielectric layer 142 does not allow that this reflection function of the light diffracted by the diffraction grating 118 is fulfilled with the layer 142 (FIG. 6E). In the case of a layer 142 made of $SiO_2$ and a core of the waveguide 104 made of germanium or made of SiGe surrounded with cladding layers made of silicon, this luminous reflection function is fulfilled with the layer 142 because a total luminous reflection takes place at the $Si/SiO_2$ interface due to the small angle of incidence of the light beam diffracted by the diffraction grating 118.

Figure 6F:
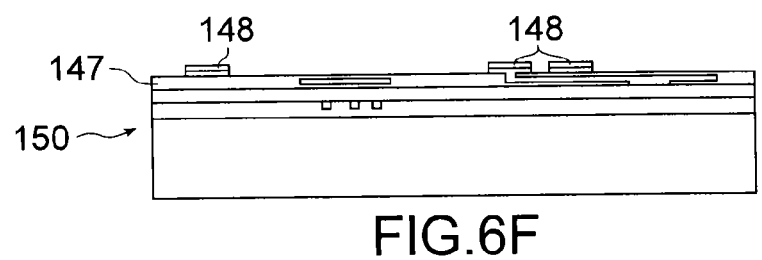
Figure 6G:
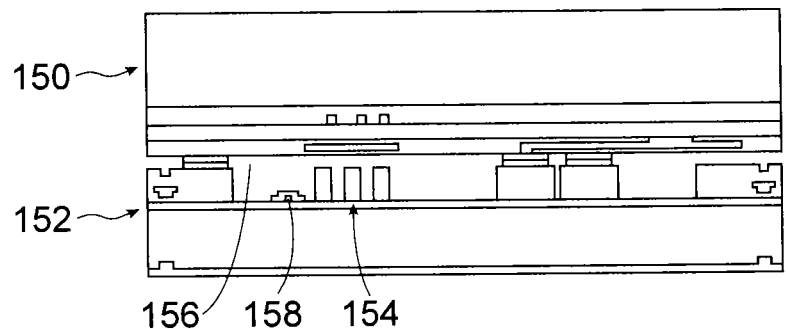
Figure 6H:
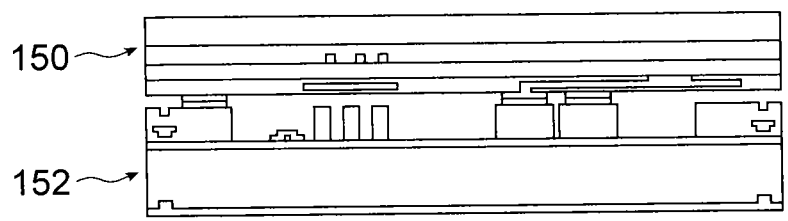
Figure 6I:
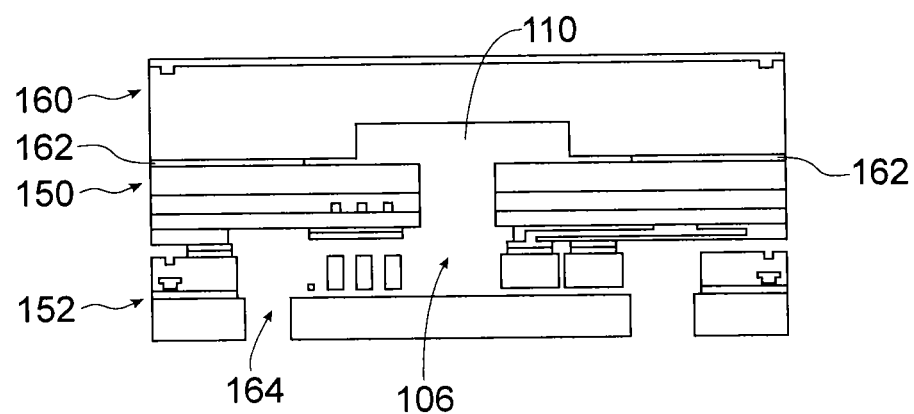

Another dielectric layer 147, for example comprising a material similar to that of the dielectric layer 142, and/or of thickness similar to that of the dielectric layer 142, is then deposited while covering the remaining portions 144, 146. A sealing layer is then formed in order to enable thereafter the second middle substrate to be made integral with the first substrate comprising the acoustic detectors. This sealing layer may correspond either to a metal layer, for example a gold-based layer of thickness equal to around 800 nm, or an aluminium-based layer of thickness equal to around 400 nm arranged on a layer of germanium of thickness equal to around 200 nm, making it possible to achieve a eutectic sealing with the semi-conductor (for example silicon) of the first substrate. Said sealing layer may also correspond to a layer of polymer for example of thickness equal to around 1 µm. As represented in FIG. 6F, said sealing layer is etched in order to only conserve sealing portions 148 at some spots. Furthermore, some remaining sealing portions are electrically connected to the remaining conductive portions 144 in order to form electrical contacts which will be electrically connected to the acoustic detectors of the device 100.

As represented in FIG. 6G, the second middle substrate 150 obtained by the implementation of the steps described previously is turned over and made integral with the first substrate, referenced 152, which comprises the acoustic detectors as well as other electrical and/or electronic elements not visible in FIGS. 6A-6I. Due to the turning over of the second middle substrate 150, the diffraction grating 118 is localised in the lower part of the core layer 126 of the waveguide 104, as described previously with reference to FIG. 3. The acoustic detectors 154, which are beam type piezoresistive microphones, are arranged near to the part of the second substrate 150 in which the chambers 106 and 108 are intended to be formed, and are electrically connected to the electrical contacts 144 formed previously. Furthermore, the detectors 154 are arranged in an etched part 156 of the first substrate 152 which will make it possible later to expose the detectors 154 to air in order that they are subjected to atmospheric pressure. Furthermore, the detectors 154 are connected to strain nanogauges 158 enabling the transformation of the pressures measured by the acoustic detectors 154 into electrical signals.

After sealing the second middle substrate 150 to the first substrate 152, the second middle substrate 150 may be thinned to the desired thickness corresponding to the desired height of the chambers 106 and 108, for example equal to 300 µm (FIG. 6H). This thinning is carried out by reducing the thickness of the bulk layer 134.

Steps of lithography and etching (for example of DRIE type) are then carried out through the second middle substrate 150 to form the chambers 106 and 108.

The light of the laser light source 102 may be injected directly into the waveguide 104, the light source 102 being in this case coupled end-to-end with the waveguide 104 via a so-called "hybrid" coupling. It is also possible to have a "heterogeneous" coupling in which the laser light source 102, for example of QCL type and made of III-V material, is transferred onto the silicon substrate. An additional structure, formed for example by lithography and etching, assures in this case the coupling between the waveguide 104 and the light source 102. The epitaxied layers of the QCL laser may be transferred onto silicon by direct bonding, as described for example in the document "Electrically driven hybrid Si/III-V Fabry-Perot lasers based on adiabatic mode transformers" of B. Ban Bakir et al., Opt. Express 2011, vol. 19, no 11, 23 May 2011.

As represented in FIG. 6I, the third upper substrate 160 is made integral on the thinned second middle substrate 150. The capillaries 110 and 112 are formed in the third upper substrate 160 prior to making this third substrate 160 integral with the second middle substrate 150. The making integral is implemented via a eutectic sealing layer, for example formed of a stack of a layer of tungsten of thickness equal to 50 nm, of a layer of tungsten nitride of thickness equal to 50 nm and a layer of gold of thickness equal to 800 nm, deposited then structured in the form of a sealing bead 162. The third substrate 160 forms especially the upper walls of the chambers 106 and 108. Thus, one of the remaining portions of the sealing layer may be used to form the upper reflective layer 122 in the first chamber 106. The eutectic sealing is carried out between the gold layer of the sealing bead 162 and the silicon (corresponding to the material of the thinned layer 134) of the second middle substrate 150.

In a variant, prior to making the third substrate 160 integral with the second substrate 150, the capillaries 110, 112 may be formed after the deposition and the structuring of the eutectic sealing layer. In this case, the upper reflective layer 122 is deposited later for example through a stencil so as to localise this layer at the part of the third upper substrate 160 intended to form the upper wall of the first chamber 106.

The inlet 114 and outlet 116 channels are formed through the first lower substrate 152. Other openings 164 are formed through the first lower substrate 152 especially so that the acoustic detectors 154 are at atmospheric pressure and form accesses for etching portions of temporary dielectric material present in the substrates, in contact especially with the acoustic detectors 154 and with the metal portions 144, 146.

In the case of the formation of the device 100 with only two substrates, the capillaries 110 and 112 are formed in the same layer as the chambers 106 and 108, that is to say in the second substrate 150. In this case, the upper reflective layer is formed via a step of metallisation with a stencil at the bottom wall of the cavity intended to form the first chamber 106, prior to the two substrates being made integral.

In the device 100 described previously, the diffraction grating 118 is dimensioned especially as a function of the wavelength of the light beam intended to be diffracted, the wavelength of the light beam being adapted as a function of the nature of the gas to be detected. The device 100 may be adapted to carry out a detection of several types of gas by forming in the device 100 several parallel waveguides which emerge on one or on two inlet faces (on each side) of the first chamber 106, each of the waveguides being coupled to a light source emitting at a different wavelength, for example between 4 µm and 5 µm, which is intended to be diffracted by the diffraction grating formed on each of the waveguides. An optical multiplexer may also be used so that the chamber 106 can receive different wavelengths, as described in the document EP 2 515 096 A1. Moreover, it is also possible that the two chambers 106 and 108 are coupled to light sources emitting for example at wavelengths different to each other, which makes it possible to excite the gas present in one or the other of the chambers 106 and 108 depending on the gas to be detected.

In the device 100 described previously, the horizontal confinement of the light beam is achieved thanks to the widening of the second end 107 of the waveguide 104. This horizontal confinement may be improved by forming trenches filled with a reflective material, for example a metal such as gold, aluminium, around the first chamber 106. These trenches are sufficiently far away, for example several tens of microns, from the first chamber 106 so as not to add to the thermal background noise, linked to the absorption of infrared radiation by the materials surrounding the excited chamber. Such trenches may be formed in the second substrate 150, for example during the etching of the chambers 106 and 108.

In the example of FIG. 1 described previously, the inlet 114 and outlet 116 channels are connected to the capillaries 110 and 112 substantially at the level of the middle of said capillaries 110, 112. In a variant, given that the device 100 is a miniaturised device formed by the implementation of microelectronic steps, said inlet 114 and outlet 116 channels may be connected to the capillaries 110 and 112 at a level other than their middle, and without perturbing the symmetry of the flow of gas in the device 100.

To increase the intensity of the signal measured by the acoustic detectors of the device 100, it is possible to place the capillaries 110, 112 at the ends of the chambers 106, 108. Such a configuration makes it possible to increase by around 5% the amplitude of the signal measured by the acoustic detectors.

The different embodiment options described in the document EP 2 515 096 A1, such as for example the use of a Peltier effect cooler, an amplifier integrated into the photoacoustic detection device, or the different examples of materials described, may apply to the photoacoustic detection device of the invention.

The invention claimed is:

1. A microelectronic photoacoustic detection device comprising
   at least one substrate comprising cavities forming a Helmholtz type differential acoustic resonator;
   acoustic detectors coupled to two of said cavities forming chambers of the resonator;
   a light source capable of emitting a light beam at at least one given wavelength;
   an optical waveguide comprising a first end optically coupled to the light source and a second end optically coupled to a first of the two chambers;
   in which the second end comprises, at an interface with the first chamber, a width of value greater than that of the width of the first end and greater than that of said at least one given wavelength, and/or in which the photoacoustic detection device comprises at least one diffraction grating arranged in the second end of the waveguide and capable of diffracting a first part of the light beam towards a lower reflective layer arranged under the second end and a second part of the light beam towards an upper reflective layer arranged at an upper wall of the first chamber.

2. Device according to claim 1, in which the ratio between the width of the second end at the interface with the first chamber and the width of the first end is greater than or equal to 3.

3. Device according to claim 1, in which the second end forms a portion of the waveguide of which the width increases from a first value equal to that of the width of the first end up to a second value equal to that of the width of the second end at the interface with the first chamber.

4. Device according to claim 3, in which the width of the second end increases on a part, called first part, of the second end of which the length is greater than or equal to around ten times the width of the second end at the interface with the first chamber.

5. Device according to claim 1, in which the diffraction grating is arranged in a part, called second part, of the second end of which the width is substantially constant and equal to that at the interface with the first chamber.

6. Device according to claim 1, in which the diffraction grating is arranged at an interface between a core layer of the waveguide and a lower cladding layer of the waveguide, the lower cladding layer being arranged between the core layer and the lower reflective layer.

7. Device according to claim 1, in which the diffraction grating is capable of diffracting the light beam such that the first or the second part of the light beam reaches, after a reflection on the lower reflective layer and/or the upper reflective layer, a bottom wall of the first chamber which is opposite to that in contact with the second end of the waveguide.

8. Device according to claim 1, in which the acoustic detectors are arranged in a first substrate and coupled to the chambers of the resonator formed in a second substrate made integral with the first substrate, volumes of the chambers communicating together via capillaries formed in a third substrate made integral with the second substrate.

9. Device according to claim 1, in which the acoustic detectors are arranged in a first substrate and coupled to the chambers of the resonator formed in a second substrate made integral with the first substrate, volumes of the chambers communicating together via capillaries formed in the second substrate, the second substrate having a thickness less than 300 µm.

10. Device according to claim 1, further comprising trenches filled with at least one optically reflective material and arranged around the first chamber.

11. Device according to claim 1, in which the two chambers comprise dimensions different to each other.

12. Device according to claim 1, in which the acoustic detectors comprise beam type piezoresistive microphones.

13. A gas detection device, comprising at least one microelectronic photoacoustic detection device according to claim 1 and further comprising gas inlet and outlet channels communicating with the chambers of the resonator and in which the wavelength intended to be emitted by the light source corresponds to an absorption wavelength of a gas intended to be detected.

14. A method of producing a microelectronic photoacoustic detection device, comprising at least the steps of:
   forming, in at least one substrate, an optical waveguide comprising a first end and a second end,
   forming a light source capable of emitting a light beam at at least one given wavelength and such that the light source is optically coupled to the first end of the waveguide,
   forming, in said at least one substrate, cavities forming a Helmholtz type differential acoustic resonator, two of said cavities forming chambers of the resonator such that a first of the two chambers is optically coupled with the second end of the waveguide,
   coupling of the acoustic detectors with the chambers of the resonator,
   in which the second end comprises, at an interface with the first chamber, a width of value greater than that of the width of the first end and greater than that of said at least one given wavelength, and/or in which the method comprises the formation of at least one diffraction grating in the second end of the waveguide capable of diffracting a first part of the light beam towards a lower reflective layer arranged under the second end and a second part of the light beam towards an upper reflective layer arranged at an upper wall of the first chamber.

* * * * *